United States Patent [19]

Petersen et al.

[11] Patent Number: 5,608,069

[45] Date of Patent: Mar. 4, 1997

[54] 1-SUBSTITUTED, 3-CARBOXYLIC ACID PIPERIDINE DERIVATIVES

[75] Inventors: Hans Petersen, Vanløse; Knud E. Andersen, Smørum; Per O. Sørensen, Frederiksberg; Jesper Lau, Farum; Henning B. Petersen, Lyngby; Behrend F. Lundt, Kokkedal, all of Denmark

[73] Assignee: Novo Nordisk A/S, Bagsvaerd, Denmark

[21] Appl. No.: 263,635

[22] Filed: Jun. 22, 1994

[30] Foreign Application Priority Data

Jun. 23, 1993 [DK] Denmark .................................. 0743/93

[51] Int. Cl.⁶ ...................... C07D 211/60; C07D 211/68; C07D 211/80
[52] U.S. Cl. ............................................. 546/194; 546/227
[58] Field of Search ..................................... 546/194, 227

[56] References Cited

FOREIGN PATENT DOCUMENTS 342635  11/1989  European Pat. Off. .
WO92/20658  11/1992  WIPO .

OTHER PUBLICATIONS

Suzdak et al., Europ. Jour. of Pharmacology, vol. 223, pp. 189–198 (1992).

*Primary Examiner*—C. Warren Ivy
*Assistant Examiner*—Raymond Covington
*Attorney, Agent, or Firm*—Steve T. Zelson, Esq.; Elias J. Lambiris, Esq.

[57] ABSTRACT

The present invention relates to therapeutically active aza-heterocyclic compounds, a method of preparing the same and to pharmaceutical compositions comprising the compounds. The novel compounds are useful in treating a central nervous system ailment related to the GABA uptake.

12 Claims, No Drawings

1-SUBSTITUTED, 3-CARBOXYLIC ACID PIPERIDINE DERIVATIVES

FIELD OF THE INVENTION

The present invention relates to novel N-substituted azaheterocyclic carboxylic acids and esters thereof in which a substituted alkyl chain forms part of the N-substituent and salts thereof, to methods for their preparation, to compositions containing them, and to their use for the clinical treatment of abnormal function of the γ-aminobutyric acid neurotransmission system.

BACKGROUND OF THE INVENTION

In recent years much pharmacological research concerning γ-aminobutyric acid (hereinafter designated GABA), an inhibitory neurotransmitter in the mammalian central nervous system, has been carried out.

The inhibition of GABA uptake results in enhanced availability of this inhibitory neurotransmitter in the synaptic cleft and thus to increased GABA'ergic activity. Increased GABA'ergic activity can be useful in the treatment, for example of anxiety, pain and epilepsy, as well as muscular and movement disorders (see, for example, P. Krogsgaard-Larsen et al., Progress in Medicinal Chemistry, 1985, 22, 68–112).

A well-known and potent inhibitor of GABA uptake from the synaptic cleft into presynaptic nerve terminals and glial cells is, for example, 3-piperidinecarboxylic acid (nipecotic acid). However, being a relatively polar compound and therefore unable to cross the blood-brain barrier, 3-piperidinecarboxylic acid itself has found no practical utility as a drug.

In U.S. Pat. No. 4,383,999 and U.S. Pat. No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as inhibitors of GABA uptake. EP 221572 claims that 1-aryloxyalkylpyridine-3-carboxylic acids are inhibitors of GABA uptake.

According to Yunger, L. M. et al., J.Pharm. Exp.Ther. 1984, 228, 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)-homo-β-proline (designated SK&F 100561) and N-(4-phenyl-4-(2-thienyl)-3-buten-1-yl)nipecotic acid (designated SK&F 100604J) are orally active inhibitors of GABA uptake. These data are summarized in Krogsgaard-Larsen, P. et al., Epilepsy Res. 1987, 1, 77–93.

DESCRIPTION OF THE INVENTION

The present invention relates to novel N-substituted azaheterocyclic carboxylic acids and esters thereof of formula I

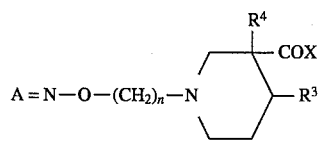

wherein A is

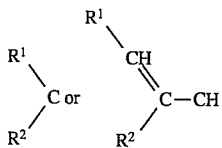

wherein
$R^1$ and $R^2$ independently are hydrogen, $C_{1-4}$-alkoxy-$C_{1-8}$-alkyl, straight or branched $C_{1-8}$-alkyl optionally substituted with either one to three halogen(s) or phenyl which phenyl group is optionally substituted with halogen, $C_{1-4}$-alkyl, $C_{1-4}$-alkoxy or trifluoromethyl; or
$R^1$ and $R^2$ independently are $C_{3-7}$-cycloalkyl or $C_{3-7}$-cycloalkenyl each of which is optionally substituted with phenyl which phenyl group is optionally substituted with halogen, $C_{1-4}$-alkyl, $C_{1-4}$-alkoxy or trifluoromethyl; or
$R^1$ and $R^2$ independently are phenyl optionally substituted with halogen, $C_{1-4}$-alkyl, $C_{1-4}$-alkoxy or trifluoromethyl;
$R^3$ and $R^4$ each represents hydrogen or may together represent a bond;
X is hydroxy or $C_{1-4}$-alkoxy;
n is 2,3,4 or 5;
provided that $R^1$ and $R^2$ are not at the same time phenyl optionally substituted with halogen, $C_{1-4}$-alkyl, $C_{1-4}$-alkoxy or trifluoromethyl when A is

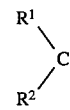

or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, phthalate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

In a preferred embodiment of the invention $R^1$ and $R^2$ independently include methyl, ethyl, n-propyl, isopropyl, methoxy, ethoxy, cyclopropyl, cyclopentyl, cyclohexyl, cyclopentenyl or cyclohexenyl, and X includes methoxy, ethoxy, isopropoxy or n-propoxy, and n includes 2 or 3.

The compounds of formula I have a greater lipophilicity—and thus a greater availability to the brain—as well as a far higher affinity to the GABA uptake sites than the parent compounds without the N-substituent (i.e. nipecotic acid and guvacine).

It has been demonstrated that the novel compounds of formula I which inhibit the uptake of GABA from the synaptic cleft possess useful pharmacological properties in the central nervous system, in that they cause a selective enhancement of GABA'ergic activity. Compounds of formula I may be used to treat for example, pain, anxiety, extrapyrimidinal dyskinesia, epilepsy and certain muscular and movement disorders. They are also useful as sedatives, hypnotics and antidepressants.

The compounds of formula I are prepared by the following methods:

Method A:

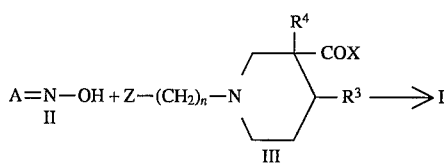

A compound of formula II wherein A is as defined above, may be reacted with a compound of formula III wherein $R^3$, $R^4$, n and X are as defined above and Z is a suitable leaving group such as halogen, p-toluene sulphonate or mesylate. This alkylation reaction may be carried out in a suitable solvent such as acetone, dibutylether, 2-butanone, tetrahydrofuran, methylisobutylketone or toluene in the presence of a base e.g. potassium carbonate at a temperature up to reflux temperature for the solvent used for e.g. 1 to 200 h.

Method B:

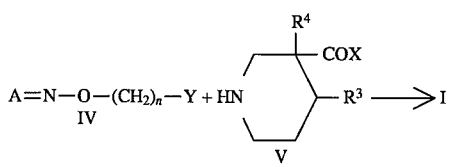

A compound of formula IV wherein A and n are as defined above and Y is a suitable leaving group such as halogen, p-toluene sulphonate or mesylate may be reacted with an azaheterocyclic compound of formula V wherein $R^3$, $R^4$ and X are as defined above. This alkylation reaction may be carried out in a solvent such as acetone, dibutylether, 2-butanone, tetrahydrofuran, methylisobutylketone or toluene in the presence of a base e.g. potassium carbonate and a catalyst, e.g. an alkali metal iodide at a temperature up to reflux temperature for the solvent used for e.g. 1 to 120 h.

Method C:

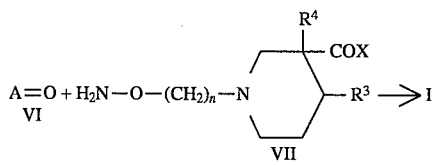

A compound of formula VI wherein A is as defined above may be reacted with an azaheterocyclic compound of formula VII wherein $R^3$, $R^4$, n and X are as defined above. This condensation reaction may be carried out in an alcoholic solvent such as ethanol in the presence of a base e.g. triethylamine at a temperature up to reflux temperature for the solvent used for e.g. 1 to 120 h.

If esters have been prepared in Methods A–C in which X is alkoxy, compounds of formula I wherein X is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II, IV, V, VI and VII may readily by prepared by methods familiar to those skilled in the art.

Compounds of formula III may be prepared according to the procedure described in EP 374801.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Synthesis" T. W. Greene and P. G. M. Wuts 2.ed. (John Wiley, 1991).

Pharmacological Methods

Values for in vitro inhibition of [$^3$H]-GABA uptake for the invention compounds were assessed essentially by the method of Fjalland (Acta Pharmacol. Toxicol. 1978, 42, 73–76).

Male wistar rat cortical tissue was gently homogenized by hand using a glass/PTFE homogenizer in 10 volumes of 0.32M sucrose. Incubation was performed in a 40 mM tris HCl buffer (pH 7.5 at 30° C.) containing 120 nM NaCl, 9.2 nM KCl, 4 mM $MgSO_4$, 2.3 nM $CaCl_2$ and 10 mM glucose, for 60 minutes at 30° C.

Values for inhibition of GABA uptake for some representative compounds are recorded in Table I.

TABLE I

| | Inhibition of [$^3$H]-GABA uptake |
|---|---|
| Example no. | IC$_{50}$ (nM) in vitro |
| 1 | >9000 |
| 2 | 236 |
| 3 | 2200 |
| 4 | 1100 |
| 5 | 2000 |
| 6 | 4500 |
| 7 | 194 |
| 8 | 960 |
| 9 | 130 |
| 10 | 790 |
| 11 | 290 |
| 12 | >3000 |
| 13 | 1040 |
| 14 | 280 |
| 15 | 920 |
| 16 | 340 |
| 17 | 79 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in pharmaceutically acceptable acid addition salt form or where possible as a metal or a lower alkylammonium salt.

This invention also relates to pharmaceutical compositions comprising a compound of formula I or a pharmaceutically acceptable salt thereof and, usually, such compositions also contains a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid such as an aqueous or nonaqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet, which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| *Mywacett ® 9-40 T | approx. 0.9 mg |

*Acylated monoglyceride used as plasticizer for film coating.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

EXAMPLES

The process for preparing compounds of formula I is further illustrated in the following examples which however are not to be construed as limiting.

Hereinafter, TLC is thin layer chromatography and THF is tetrahydrofuran, CDCl$_3$ is deuterio chloroform and DMSO-d$_6$ is hexadeuterio dimethylsulfoxide. The structures of the compounds are confirmed by either elemental analysis or NMR, where peaks assigned to characteristic protons in the title compounds are presented where appropriate. NMR shifts (δ) are given in parts per million (ppm). M.p. is melting point and is given in °C. Column chromatography was carried out using the technique described by W. C. Still et al, J. Org. Chem. 1978, 43, 2923–2925 on Merck silica gel 60 (Art. 9385). Compounds used as starting materials are either known compounds or compounds which can readily be prepared by methods known per se.

EXAMPLE 1

E-(R )-1-(2-((((2-Methylphenyl)methylene)amino)oxy)ethyl)-3-piperidinecarboxylic acid hydrochloride A mixture of 2-methylbenzaldehyde (10.8 g, 90 mmol), hydroxylammonium chloride (9.4 g, 135 mmol), sodium hydroxide (18.0,0.45 mol), ethanol (80 ml) and water (20 ml) was heated at reflux for 1 h. A solution of citric acid (20 g) in water (700 ml) was added and the mixture was left for crystallisation. The precipitate was collected and recrystallised from water to give 8.6 g of 2-methylbenzaldehyde oxime. M.p. 49.0–49.4° C.

A mixture of the above oxime (2.0 g, 15 mmol), (R)-1-(2-bromoethyl)-3-piperidinecarboxylic acid (5.2 g, 15 mmol), potassium carbonate (6.2 g, 45 mmol) and acetone (100 ml) was heated at reflux for 2 days. The mixture was filtered and the solvent was evaporated from the filtrate in vacuo. The residue was purified by column chromatography on silica gel (75 g, n-heptane/ethyl acetate 10/1). The crude ester was dissolved in toluene (50 ml), then methanol (0.35 ml) and chlorotrimethylsilane (1.10 ml) was added and the mixture was left for crystallisation. The precipitate was collected to give 2.40 g of E-(R)-1-(2-((((2-methylphenyl)methylene)amino)oxy)ethyl)-3-piperidinecarboxylic acid ethyl ester hydrochloride. M.p. 83.5°–86.0° C.

The above ester (2.22 g, 6.3 mmol) was dissolved in a mixture of ethanol (65 ml) and 12N sodium hydroxide (4.9 ml) and stirred at ambient temperature for 1 h. Water (20 ml) was added and the mixture extracted with diethyl ether (3×30 ml). The phases were separated and pH in the aqueous phase was adjusted to 5 with 2N hydrochloric acid. The aqueous phase was extracted with dichloromethane (2×40 ml) and the solvent was evaporated from the combined organic phases in vacuo. The residue was dissolved in toluene (25 ml), then methanol (0.17 ml) and chlorotrimethylsilane (0.52 ml) were added and the mixture left for crystallisation. This afforded 0.51 g of the title compound as a solid. M.p. 108.5°–109.9° C.

$^1$H-NMR (DMSO-d$_6$) δ 4.73 (m,2H).

EXAMPLE 2

(R) -1-(2-((((4-Methyl-2-phenyl-2-penten-1-ylidene)amino)oxy)ethyl)-3-piperidinecarboxylic acid To a solution of 4-methyl-2-phenyl-2-pentenal (5.0 g, 29 mmol) and hydroxylammonium chloride (2.5 g, 36 mmol) in a mixture of absolute ethanol (15 ml) and water (5 ml) was carefully added a solution of sodium carbonate (7.3 g, 69 mmol) in water (20 ml). After stirring for 5 h a precipitate was filtered off and dried in the air. The crude product was purified by column chromatography on silica gel (50 g, cyclohexane/ethyl acetate 3/1) to give 3.2 g of 4-methyl-2-phenyl-2-pentenal oxime as a solid. M.p. 107°–110° C.

A mixture of the above oxime (1.9 g, 10 mmol), (R)-1-(2-bromoethyl)-3-piperidinecarboxylic acid hydrobromide (3.5 g, 10 mmol), potassium carbonate (4.2 g, 30 mmol) and acetone (25 ml) was stirred at ambient temperature for 16 h. The mixture was filtered and the solvent was evaporated from the filtrate in vacuo. The residue was purified by column chromatography on silica gel (75 g, cyclohexane/ethyl acetate 3/2) to give 1.6 g of (R)-1-(2(-(((4-methyl-2-phenyl-2-penten-1-ylidene)amino)oxy)ethyl)-3-piperidinecarboxylic acid ethyl ester.

The above ester (0.8 g, 2.1 mmol) was dissolved in a mixture of 96% ethanol (5 ml) and 10N sodium hydroxide (0.4 ml) and stirred at ambient temperature for 3 h. Then pH in the aqueous phase was adjusted to 2 with concentrated hydrochloric acid and the mixture was extracted with dichloromethane (3×100 ml). The organic phase was dried (MgSO$_4$) and the solvent was evaporated in vacuo. This afforded 0.65 g of the title compound as a foam.

Calculated for C$_{20}$H$_{28}$N$_2$O$_3$.HCl.1.25 H$_2$O:
C,59.5%;H,7.9%;N,6.9%; Found: C,59.6%;H,7.8%;N, 6.8%.

EXAMPLE 3

Z-(R)-1-(2-(((1-Phenyl-1-octanylidene)amino)oxy) ethyl)-3-piperidinecarboxylic acid hydrochloride A mixture of octanophenone (19.0 g, 93 mmol), hydroxylammoniumchloride (12.9 g, 186 mmol) and anhydrous pyridine (100 ml) was heated at reflux for 16 h. The reaction mixture was allowed to cool to ambient temperature and the solvent was evaporated in vacuo. To the residue was added 5% aqueous tartaric acid (100 ml) and the mixture was extracted with ethyl acetate (3×100 ml). The combined organic phases were washed with brine (30 ml) and dried (Na$_2$SO$_4$). The solvent was evaporated in vacuo and the residue was purified by column chromatography on silica gel (375 g, n-heptane/ethyl acetate 9/1) to give 14.6 g of the Z-octanophenone oxime. M.p. 51°–52° C.

A mixture of the above oxime (13.0 g, 59 mmol), 1,2-dibromoethane (102 ml), potassium carbonate (8.19 g, 178 mmol) and 4-methyl-2-pentanone was heated at reflux for 60 h. The mixture was filtered and the solvent was evaporated from the filtrate in vacuo. To the residue was added toluene (200 ml), 1,2-dibromoethane (50 ml), N,N,N,N-tetrabutylammonium bromide (1.91 g, 5.9 mmol) and 12N sodium hydroxide (250 ml). The mixture was stirred at ambient temperature for 3 days. The phases were separated and the aqueous phase was extracted with toluene (200 ml). To the combined toluene phases were added water (100 ml) and pH in the aqueous phase was adjusted to 5.5 with 2N hydrochloric acid. The organic phase was dried (Na$_2$SO$_4$) and the solvent was evaporated in vacuo to give 16.6 g octanophenone O-(2-bromoethyl)oxime as the Z-isomer containing a small amount of the E-isomer.

A mixture of the above bromide (16.0 g, 49 mmol), (R)-3-piperidinecarboxylic acid ethyl ester (+)-tartrate (30.1 g, 98 mmol), potassium carbonate (40.7 g, 294 mmol) and 4-methyl-2-pentanone (200 ml) was heated at 90° C. for 2 days. The mixture was filtered and the solvent was evaporated from the filtrate in vacuo. The residue was purified by column chromatography on silica gel (500 g, n-heptane/ ethyl acetate 8/2) to give 12.3 g of Z-(R)-1-(2-(((1-phenyl-1-octanylidene)amino)oxy)ethyl)-3-piperidinecarboxylic acid ethyl ester and 0.4 g of E-(R)-1-(2-(((1-phenyl-1-octanylidene)amino)-oxy)ethyl)-3-piperidinecarboxylic acid ethyl ester.

The Z-isomer of the above ester (10.0 g, 25 mmol) was dissolved in ethanol (100 ml) and 12N sodium hydroxide (9 ml) was added. The mixture was stirred at room temperature for 2 h, then neutralised with 4N hydrochloric acid and concentrated to dryness in vacuo. The residue was dissolved in ethyl acetate (200 ml) and extracted with water (40 ml). The aqueous phase was extracted with ethyl acetate (100 ml). The combined organic phases were washed with brine and dried (Na$_2$SO$_4$). The solvent was evaporated in vacuo and the residue dissolved in toluene (33 ml). The mixture was heated at 40° C. and chlorotrimethylsilane (2.92 g, 27 mmol) was added followed by methanol (0.3 g, 9 mmol). The mixture was allowed to cool to room temperature and left for crystallisation. The precipitate was collected, recrystallised from water and dried in vacuo. This afforded 3.63 g of the title compound as a solid. M.p. 127°–128° C.

$^1$H-NMR (DMSO-d$_6$) δ 4.58 (m,2H).

EXAMPLE 4

E-(R)-1-(2-(((1-Phenyl-1-octanylidene)amino)oxy) ethyl)-3-piperidinecarboxylic acid hydrochloride A mixture of E-(R)-1-(2-(((1-phenyl-1-octanylidene)amino)oxy)ethyl)-3-piperidinecarboxylic acid ethyl ester (0.3 g, 0.75 mmol, prepared as described in example 3), ethanol (5 ml) and 12N sodium hydroxide (0.27 ml) was stirred at ambient temperature for 2 h, then neutralised with 4N hydrochloric acid and concentrated to dryness in vacuo. The residue was dissolved in ethyl acetate (70 ml) and washed with water (20 ml). The aqueous phase was extracted with ethyl acetate (50 ml), the combined organic phases were washed with brine and dried (Na$_2$SO$_4$). The solvent was evaporated in vacuo and the residue dissolved in toluene (3 ml). The mixture was heated to 40° C. and then added to a freshly prepared solution of chloro trimethylsilane (40 µl) and methanol (4 µl) in toluene (0.14 ml). The mixture was allowed to cool to room temperature and the solvent was evaporated in vacuo. This afforded 0.13 g of the title compound as an oil. $^1$H-NMR (DMSO-d$_6$) δ 4.32 (m,2H).

EXAMPLE 5

Z-(R)-1-(2-(((2-Methoxy-1-phenyl-1-ethylidene)amino)oxy)ethyl)-3-piperidinecarboxylic acid hydrochloride A mixture of hydroxylammonium chloride (10.0 g, 144 mmol) and sodium hydroxide (6.0 g, 150 mmol) in absolute ethanol (200 ml) was stirred for 1 h. The precipitated sodium chloride was filtered off and 2-methoxyacetophenone (10.0 g, 67 mmol) was added to the filtrate. The mixture was heated at reflux for 30 min. The precipitated compound was collected and recrystallised from n-heptane/ethanol 9/1 to give 7.1 g 2-methoxyacetophenone oxime.

A mixture of the above oxime (5.5 g, 33 mmol), 1,2-dibromoethane (50 ml), potassium carbonate (12.4 g, 90 mmol) and acetone (100 ml) was heated at reflux for 24 h. The mixture was filtered and the solvent was evaporated from the filtrate in vacuo. The residue was purified by column chromatography on silica gel (80 g, n-heptane/ethyl acetate 20/1) to give 6.6 g of 2-methoxyacetophenone O-(2-bromoethyl)oxime.

A mixture of the above bromide (6.6 g, 24 mmol), (R)-3-piperidinecarboxylic acid ethyl ester (+)-tartrate (4.5 g, 29 mmol), potassium carbonate (5.0 g, 36 mmol) and acetone (100 ml) was heated at reflux for 2 days. The mixture was filtered and the solvent was evaporated from the filtrate in vacuo. The residue was dissolved in ethyl acetate (100 ml) and the resulting mixture washed with water (50 ml) and saturated ammonium chloride (10 ml). The organic phase was dried (MgSO$_4$) and the solvent evaporated in vacuo to give 7.8 g of Z-(R)-1-(2-(((2-methoxy-1-phenyl-1-ethylidene)amino)oxy)-ethyl)-3-piperidinecarboxylic acid ethyl ester.

A mixture of the above ester (7.8 g, 22 mmol), ethanol (50 ml) and 2N sodium hydroxide (50 ml) was heated at reflux for 1 h, then cooled to room temperature and extracted with n-heptane (100 ml). The aqueous phase was acidified with concentrated hydrochloric acid, extracted with dichloromethane (2×50 ml) and the solvent was evaporated from the organic phase in vacuo. This afforded 1.6 g of the title compound.

$^1$H-NMR (CDCl$_3$) δ 3.30 (s,3H).

EXAMPLE 6

Z-(R)-1-(2-(((1-Phenyl-2,2,2-trifluoro-1-ethylidene)amino)oxy)ethyl)-3-piperidinecarboxylic acid hydrochloride A mixture of hydroxylammonium chloride (13.9 g, 200 mmol) and 2,2,2-trifluoroacetophenone (17.4 g, 92 mmol) in absolute ethanol (150 ml) was heated at reflux for 1 h and then stirred at ambient temperature for 16 h. The solvent was evaporated in vacuo, the residue suspended in water (100 ml), filtered and washed with water (20 ml), n-heptane (20 ml) and dried to give 14.0 g 2,2,2-trifluoroacetophenone oxime.

A mixture of the above oxime (13.5 g, 71 mmol), 1,2-dibromoethane (65 ml), potassium carbonate (29.4 g, 213 mmol) and acetone (100 ml) was heated at reflux for 16 h and then stirred at room temperature for 7 days. The mixture was filtered and the solvent was evaporated from the filtrate in vacuo to give 20.7 g of 2,2,2-trifluoroacetophenone O-(2-bromoethyl)oxime.

A mixture of the above bromide (20.0 g, 68 mmol), (R)-3-piperidinecarboxylic acid ethyl ester (+)-tartrate (30.7 g, 100 mmol), potassium carbonate (28.0 g, 203 mmol), sodium iodide (1.0 g, 7 mmol) and acetone (200 ml) was heated at reflux for 2 h and then stirred at ambient temperature for 16 h. The mixture was filtered and the solvent was evaporated from the filtrate in vacuo. Water (200 ml) was added and the mixture extracted with dichloromethane (3×50 ml). The combined organic phases were dried (MgSO$_4$) and the solvent was evaporated in vacuo to give 38.8 g of crude Z-(R)-1-(2-(((1-phenyl-2,2,2-trifluoro-1-ethylidene)amino)oxy)ethyl)-3-piperidinecarboxylic acid ethyl ester.

A mixture of the above crude ester (38.0 g), ethanol (150 ml), 9N sodium hydroxide (25 ml) and water (125 ml) was stirred at ambient temperature for 4 h and the volume then concentrated to one third. Concentrated hydrochloric acid (32 ml) was added and the mixture was extracted with dichloromethane (2×50 ml). The combined organic phases were dried (MgSO$_4$) and filtered. The filtrate was left for crystallisation. This afforded 24.3 g of the title compound.

$^1$H-NMR (DMSO-d$_6$) δ 4.65 ppm (m,2H).

EXAMPLE 7

Z-(R)-1-(2-(((1-(Cyclopenten-1-ylphenylmethylene)amino)oxy)ethyl)-3-piperidinecarboxylic acid hydrochloride A mixture of cyclopentylphenylmethanone (15.0 g, 86 mmol), hydroxyl ammonium chloride (12.0 g, 172 mmol) and anhydrous pyridine (90 ml) was heated at reflux for 16 h. The reaction mixture was allowed to cool to room temperature and the solvent evaporated in vacuo. To the residue was added 10% aqueous citric acid (100 ml) and the mixture was extracted with ethyl acetate (100 ml). The organic phase was washed with 10 % aqueous citric acid (50 ml), brine (25 ml) and dried (Na$_2$SO$_4$). The solvent was evaporated in vacuo. The residue was dissolved in cyclohexane (100 ml) and left for crystallisation. The precipitate was collected and washed with cyclohexane to give 5.8 g of the crude cyclopenten-1-ylphenylmethanone oxime as an amorphous solid.

A mixture of the above oxime (2.0 g, 11 mmol), 1,2-dibromoethane (9.1 ml), N,N,N,N-tetrabutylammonium bromide (0.34 g, 1 mmol) and 12N sodium hydroxide (10 ml) was stirred vigorously at ambient temperature for 4 h. Water (50 ml), 4 N hydrochloric acid (50 ml) and diethylether (50 ml) were added and the phases were separated. The aqueous phase was extracted with diethylether (30 ml). The combined organic phases were washed with excess 5% aqueous sodium hydrogencarbonate, brine (25 ml) and dried (Na$_2$SO$_4$). The solvent was evaporated in vacuo to give 2.8 g of the crude cyclopenten-1-yl-phenyl O-(2-bromoethyl)oxime.

A mixture of the above bromide (2.8 g, 9.5 mmol), (R)-3-piperidinecarboxylic acid ethyl ester (+)-tartrate (5.8 g, 19 mmol), potassium carbonate (10.4 g, 76 mmol) and 4-methyl-2-pentanone (100 ml) was heated at reflux for 85 h and then stirred at ambient temperature for 9 days. The mixture was filtered and the solvent was evaporated from the filtrate in vacuo. The residue was dissolved in ethyl acetate (50 ml), water (40 ml) was added and pH in the aqueous phase was adjusted to 4 with 34% aqueous tartaric acid. The phases were separated and the organic phase extracted with water (20 ml), then twice with 34% aqueous tartaric acid (8 ml+5 ml). The combined aqueous phases were diluted to the triple volume, pH adjusted to 8 with 2 N sodium hydroxide and extracted with ethyl acetate (50 ml). The organic phase was washed with brine (10 ml) and dried (Na$_2$SO$_4$). The solvent was evaporated in vacuo to give 2.2 g of (R)-1-(2-(((cyclopenten-1-ylphenyl-methylene)amino)oxy)ethyl)-3-piperidinecarboxylic acid ethyl ester.

A mixture of the above ester (2.0 g, 5.4 mmol), ethanol (50 ml) and 4N sodium hydroxide (6 ml) was stirred at ambient temperature for 16 h and then concentrated in vacuo. The residue was dissolved in dichloromethane (200 ml) and cooled on an icebath. Concentrated hydrochloric acid (2.9 ml) was carefully added, the precipitated sodium chloride was dissolved with ice and the organic phase dried (Na$_2$SO$_4$). The solvent was evaporated in vacuo. This afforded 1.71 g of the title compound as a solid. M.p. 193–195° C.

$^1$H-NMR (DMSO-d$_6$) δ 4.40 (m,2H).

EXAMPLE 8

(R)-1-(2-(((Cyclopropylphenylmethylene) amino)oxy)ethyl)-3-piperidinecarboxylic acid hydrochloride To a suspension of (R)-1-(2-bromoethyl)-3-piperidinecarboxylic acid ethyl ester hydrobromide (6.90 g, 20 mmol) and triethylamine (4.04 g, 40 mmol) in DMF (30 ml) was added N-hydroxyphthalimide (3.26 g, 20 mmol). The mixture was stirred for 5 h, filtered and the solvent was evaporated from the filtrate in vacuo. The residue was dissolved in dichloromethane (50 ml) and the resulting mixture washed with 10% aqueous potassium carbonate (3×20 ml) and water (20 ml). The solvent was evaporated in vacuo and the residue crystallised from absolute ethanol (25 ml). The precipitate was collected, washed with cold absolute ethanol and dried in vacuo to give 3.3 g of (R)-1-(2-((phthalimido)oxy)ethyl)-3-piperidinecarboxylic acid ethyl ester.

A mixture of the above ester (3.3 g, 10 mmol), acetic acid (7 ml) and concentrated hydrochloric acid (4.2 ml) was heated at 80° C. for 1.5 h. The reaction mixture was cooled to 5° C., filtered and the filterpad washed with cold acetic acid (2×2 ml). The solvent was evaporated from the filtrate in vacuo and the residue was dissolved in warm absolute ethanol (10 ml) and left for crystallisation. The precipitate was collected and dried in vacuo to give 1.1 g of (R)-1-(2-((amino)oxy)ethyl)-3-piperidinecarboxylic acid dihydrochloride.

To a solution of the above acid dihydrochloride (1.04 g, 4 mmol) in absolute ethanol (10 ml) was added triethylamine (1.11 g, 11 mmol) and the resulting mixture was cooled on an icebath. The precipitate was filtered off and the filterpad washed with ethanol (5 ml). The solvent was evaporated from the combined filtrates and the residue was dissolved in absolute ethanol (5 ml). Cyclopropyl phenylketone (0.58 g, 4 mmol) was added and the mixture heated to 70° C. for 3 days. The solvent was evaporated in vacuo and the residue purified by column chromatography on silica gel (200 g, chloroform/methanol 3/2) to give 0.23 g of the title compound as an oil.

$^1$H-NMR (CDCl$_3$) δ 4.35 (dd,2H).

EXAMPLE 9

(R)-1-(2-(((1,2-Diphenylethylidene)amino)oxy)ethyl)-3-piperidinecarboxylic acid hydrochloride A mixture of 1,2-diphenylethanone (19.6 g, 100 mmol) and hydroxyl ammonium chloride (13.9 g, 200 mmol) in absolute ethanol (200 ml) was heated at reflux for 4 h. The solvent was evaporated in vacuo and the residue extracted with dichloromethane (2×100 ml). The combined organic phases were washed with water (2×50 ml) and brine (10 ml) and dried (MgSO$_4$). The solvent was evaporated in vacuo and the residue left for crystallisation. The crystallised product was suspended in n-heptane/diethylether 20/1 and the precipitate collected to give 5.1 g of 1,2-diphenylethanone oxime.

A suspension of the above oxime (5.0 g, 24 mmol), 1,2-dibromoethane (25 ml) and potassium carbonate (10.0 g, 72 mmol) in acetone (25 ml) was heated at reflux for 1 h, then stirred at ambient temperature for 72 h and finally heated at reflux for 4.5 h. Potassium iodide (0.5 g) was added and refluxing continued for an additional 16 h. Water (100 ml) was added and the resulting mixture extracted with dichloromethane (2×100 ml). The combined organic phases were washed with water (100 ml) and brine (10 ml) and dried (MgSO$_4$). The solvent was evaporated in vacuo and the residue was purified by column chromatography on silica gel (60 g, n-heptane/ethyl acetate 10/1) to give 3.6 g of 1,2-diphenylethanone O-(2-bromoethyl)oxime.

A mixture of the above bromide (3.5 g, 11 mmol), (R)-3-piperidinecarboxylic acid ethyl ester (3.1 g, 20 mmol), potassium carbonate (4.1 g, 30 mmol), sodium iodide (0.15 g, 1 mmol) and acetone (100 ml) was heated at reflux for 16 h. Water (100 ml) was added and the resulting mixture was extracted with dichloromethane (2×100 ml). The combined organic phases were washed with water (100 ml) and brine (10 ml) and dried (MgSO$_4$). The solvent was evaporated in vacuo to give 5.0 g crude (R)-1-(2-(((1,2-diphenylethylidene)amino)oxy)ethyl)-3-piperidinecarboxylic acid ethyl ester.

The above crude ester (5.0 g, 15 mmol) was dissolved in a mixture of 96% ethanol (25 ml), 9N sodium hydroxide (2.5 ml) and water (20 ml) and stirred at ambient temperature for 16 h. The volume of the mixture was reduced in vacuo to 20 ml and pH in the aqueous phase was adjusted to 2 with 3N hydrochloric acid. The resulting mixture was extracted with dichloromethane (2×25 ml). The combined organic phases were dried (MgSO$_4$) and the solvent was evaporated in vacuo. This afforded 3.3 g of the title compound.

$^1$H-NMR (DMSO-d$_6$) δ 4.20 (s,2H).

EXAMPLE 10

(R)-1-(2-(((2-Phenyl-2-penten-1-ylidene)amino)oxy)ethyl)-3-piperidinecarboxylic acid hydrochloride A mixture of hydroxylammonium chloride (10.84 g, 0.156 mol) and potassium carbonate (21.56 g, 156 mmol) in absolute ethanol (100 ml) was stirred for 2 h. The precipitated sodium chloride was filtered off and 2-phenyl-2-pentenal (5.00 g, 31 mmol) was added to the filtrate. The mixture was stirred at ambient temperature for 16 h. The solvent was evaporated in vacuo, the residue was crystallised from aqueous ethanol to give 4.09 g 2-phenyl-2-pentenal oxime.

A mixture of the above oxime (2.0 g, 11 mmol), (R)-1-(2-bromoethyl)-3-piperidinecarboxylic acid ethyl ester hydrobromide (3.94 g, 11 mmol), potassium carbonate (4.73 g, 34 mmol) and acetone (25 ml) was stirred at room temperature for 4 days. The mixture was filtered and the solvent was evaporated from the filtrate in vacuo. The residue was purified by column chromatography on silica gel (75 g, cyclohexane/ethyl acetate 3/1) to give 2.08 g of (R)-1-(2-(((2-phenyl-2-penten-1-ylidene)amino)oxy)ethyl)-3-piperidinecarboxylic acid ethyl ester.

The above ester (1.0 g, 2.7 mmol) was dissolved in a mixture of 96% ethanol (7.5 ml) and 4N sodium hydroxide (2.8 ml) and stirred at ambient temperature for 18 h. The ethanol was removed in vacuo and the residue cooled on an ice-bath. Concentrated hydrochloric acid (1.16 ml) was added and the mixture was extracted with dichloromethane (150 ml). The organic phase was dried (MgSO$_4$) and the solvent evaporated in vacuo. This afforded 0.95 g of the title compound as a foam.

Calculated for $C_{19}H_{26}N_2O_3 \cdot HCl \cdot 1.25\ H_2O$
C,61.45%;H,7.46%;N,7.54%; Found:
C,61.27%;H,7.84%;N,7.70%.

EXAMPLE 11

(R)-1-(2-((((5-Methyl-2-phenyl-2-hexen-1-ylidene)amino)oxy)ethyl)-3-piperidinecarboxy acid hydrochloride To a solution of 5-methyl-2-phenyl-2-hexenal (5.0 g, 27 mmol) and hydroxylammonium chloride (3.7 g, 53 mmol) in a mixture of 96% ethanol (20 ml) and water (5 ml) was carefully added a solution of sodium carbonate (11.2 g, 106 mmol) in water (30 ml). The resulting mixture was stirred for 2h, the precipitated compound was filtered off and suspended in dichloromethane (500 ml). The suspension was filtered and the solvent evaporated from the filtrate in vacuo to give 4.1 g of 5-methyl-2-phenyl-2-hexenal oxime.

A mixture of the above oxime (2.0 g, 10 mmol), (R)-1-(2-bromoethyl)-3-piperidinecarboxylic acid ethyl ester hydrobromide (3.4 g, 10 mmol), potassium carbonate (4.7 g, 34 mmol) and acetone (25 ml) was stirred at room temperature for 4 days. The mixture was filtered and the solvent was evaporated from the filtrate in vacuo. The residue was purified by column chromatography on silica gel (75 g, cyclohexane/ethyl acetate, gradient 3/1 to 2/1) to give 1.3 g of (R)-1-(2-(((5-methyl-2-phenyl-2-hexen-1-ylidene)amino)oxy)ethyl)-3- piperidinecarboxylic acid ethyl ester.

The above ester (0.54 g, 1.4 mmol) was dissolved in a mixture of 96% ethanol (5 ml) and 4N sodium hydroxide (1.4 ml) and stirred at ambient temperature for 18 h. The ethanol was removed in vacuo and the residue cooled on an ice-bath. Concentrated hydrochloric acid (0.58 ml) was added and the mixture was extracted with dichloromethane (3×100 ml). The organic phase was washed with water (3 ml), dried (MgSO$_4$) and and the solvent evaporated in vacuo. This afforded 0.55 g of the title compound as a foam.

$^1$H-NMR (CDCl3) δ 6.05 (t, 1H).

EXAMPLE 12

(R) -1-(2-(((5-Methoxy-1-phenyl-1-pentylidene)amino)oxy)ethyl)-3-piperidinecarboxylic acid hydrochloride A mixture of 1,4-dibromobutane (216 g, 1 mol), methanol (45 ml) and toluene (45 ml) was heated at reflux under an inert atmosphere. A solution of sodium methoxide prepared from sodium (15.3 g, 0.7 mol) and methanol (225 ml) was added over a period of 3 hours while the mixture was kept at reflux. When addition was complete the reaction mixture was kept at reflux for an additional hour and the solvent then distilled off. Water (200 ml) was added, the resulting mixture extracted with diethylether (2×300 ml) and the combined organic phases were dried ($Na_2SO_4$). The solvent was evaporated in vacuo and the residue was submitted to fractional distillation to give 33.7 g of 1-bromo-4-methoxybutane. B.p. 76°–78° C./35 mmHg.

A mixture of the above bromide (30.0 g, 180 mmol), potassium cyanide (23.4 g, 360 mmol), water (6 ml) and methanol (40 ml) was heated at reflux for 3.5 hours and then stirred at ambient temperature for 64 hours. After filtration, water (25 ml) was added to the filtrate and the resulting mixture was extracted with diethylether (3×50 ml). The combined organic phases were washed with brine (20 ml) and dried ($Na_2SO_4$). The solvent was evaporated in vacuo and the residue submitted to fractional distillation to give 10.6 g of 4-methoxypentanecarbonitrile. B.p. 103° C./35 mmHg.

To a solution of phenylmagnesium bromide (16.0 g, 88 mmol) in anhydrous diethylether (55 ml) under an atmosphere of nitrogen was dropwise added a solution of the above nitrile (10.0 g, 88 mmol) in anhydrous diethylether while the temperature was allowed to raise to reflux. The reaction mixture was heated at reflux for 5 h and then stirred at room temperature for 16 h. A 4N hydrochloric acid solution (50 ml) was carefully added and the mixture stirred at ambient temperature for 4 h. The phases were separated and the aqueous phase extracted with diethylether (2×50 ml). The combined organic phases were washed with 5% sodium hydrogencarbonate (25 ml) and dried ($Na_2SO_4$). The solvent was evaporated in vacuo and the residue submitted to fractional distillation to give 9.1 g of 5-methoxy-1-phenyl-1-pentanone. B.p. 127°–130° C./5 mmHg.

A mixture of the above ketone (8.8 g, 46 mmol), hydroxylammonium chloride (5.5 g, 78 mmol) and anhydrous pyridine (50 ml) was heated at reflux for 16 h. The reaction mixture was allowed to cool to room temperature and the solvent then evaporated in vacuo. To the residue was added 10% aqueous citric acid (100 ml) and the mixture was extracted with ethyl acetate (100 ml+50 ml). The combined organic phases were washed with 10% aqueous citric acid (25 ml), brine (25 ml) and dried ($Na_2SO_4$). The solvent was evaporated in vacuo and the residue purified by column chromatography on silica gel (250 g, n-heptane/ethyl acetate gradient ¼ to ½ to give 7.25 g of Z-5-methoxy-1-phenyl-1-pentanone oxime as a colourless oil.

A mixture of the above oxime (6.5 g, 31 mmol), 1,2-dibromoethane (27 ml, 31 mmol), N,N,N,N-tetrabutylammonium bromide (0.96 g, 3 mmol) and 12N sodium hydroxide (30 ml) was cooled on an icebath with vigorous stirring until the initial exotherm had subsided. The mixture was then stirred at ambient temperature for 16 h. Water (50 ml), 4 N hydrochloric acid (50 ml) and dichloromethane (100 ml) were added and the phases were separated. To the organic phase was added water (50 ml) and pH in the aqueous phase adjusted to 5 with 10% aqueous citric acid. The organic phase was washed with water (50 ml), brine (25 ml) and dried ($Na_2SO_4$). The solvent was evaporated in vacuo to give 9.1 g of 5-methoxy-1-phenyl-1-pentanone O-(2-bromoethyl)oxime.

A mixture of the above bromide (4.6 g, 15 mmol), (R)-3-piperidinecarboxylic acid ethyl ester (+)-tartrate (8.9 g, 29 mmol), potassium carbonate (12.0 g, 87 mmol) and 4-methyl-2-pentanone (100 ml) was heated at reflux for 22 h. The mixture was filtered and the solvent was evaporated from the filtrate in vacuo. The residue was dissolved in ethyl acetate (75 ml), extracted with acidic water (2×75 ml) adjusted to pH 4 with 34% aqueous tartaric acid and the phases were separated. The organic phase was extracted with 34% tartaric acid (2×10 ml) and the combined aqueous extracts were diluted to 70 ml with water. Ethyl acetate (50 ml) was added and pH in the aqueous phase was adjusted to 9 with 4N sodium hydroxide. The organic phase was washed with brine (10 ml) and dried ($Na_2SO_4$). The solvent was evaporated in vacuo to give 2.6 g of Z-(R)-1-(2-(((5-methoxy-1-phenyl-1-pentylidene)amino)oxy)ethyl)-3-piperidinecarboxylic acid ethyl ester.

A solution of the above ester (2.5 g, 6.4 mmol), ethanol (40 ml) and 4N sodium hydroxide (7.2 ml) was stirred at ambient temperature for 16 h. The solvent was evaporated in vacuo, the residue dissolved in dichloromethane (150 ml) and cooled on an icebath. Concentrated hydrochloric acid (3.5 ml) was added, the precipitated sodium chloride dissolved with a minimal amount of ice, the organic phase dried ($Na_2SO_4$) and the solvent was evaporated in vacuo. This afforded 2.3 g of the title compound as a foam.

$^1$H-NMR (DMSO-$d_6$) δ 4.55 (m,2H).

EXAMPLE 13

(R)-1-(2-(((1,3-Diphenylprop-2-ylidene)amino)oxy)ethyl)-3-piperidinecarboxylic acid hydrochloride To a solution of 1,3-diphenyl-2-propanone (5.0 g, 24 mmol) and hydroxylammonium chloride (3.3 g, 48 mmol) in a mixture of absolute ethanol (30 ml) and water (10 ml) was carefully added a solution of sodium carbonate (13.2 g, 96 mmol) in water (30 ml). The resulting mixture was stirred at room temperature for 16 h. The precipitated compound was collected and washed with water (3×15 ml) and dried to give 4.9 g of 1,3-diphenyl-2-propanone oxime.

A mixture of the above oxime (3.0 g, 13 mmol), (R)-1-(2-bromoethyl)-3-piperidinecarboxylic acid ethyl ester hydrobromide (4.6 g, 13 mmol), potassium carbonate (5.4 g, 39 mmol) and acetone (40 ml) was stirred at room temperature for 3 days. The mixture was filtered and the solvent was evaporated from the filtrate in vacuo. The residue was purified by column chromatography on silica gel (50 g, cyclohexane/ethyl acetate 3/1) to give 1.8 g of (R)-1-(2-(((1,3-diphenylpropan-2-ylidene)amino)oxy)ethyl)-3-piperidinecarboxylic acid ethyl ester.

The above ester (0.5 g, 1.2 mmol) was dissolved in a mixture of absolute ethanol (2.7 ml) and 4N sodium hydroxide (1.0 ml) and stirred at ambient temperature for 24 h. The ethanol was removed in vacuo and the residue cooled on an icebath. Concentrated hydrochloric acid (0.4 ml) and water (1.5 ml) were added and the mixture was extracted with dichloromethane (50 ml). The organic phase was dried ($MgSO_4$) and the solvent evaporated in vacuo. This afforded 0.37 g of the title compound as a foam.

$^1$H-NMR (DMSO-$d_6$) δ 4.30 (brs,2H).

EXAMPLE 14

(R)-1-(2-(((1-Phenyl-3-methyl-1-butylidene)amino)oxy)ethyl)-3-piperidinecarboxylic acid hydrochloride A mixture of 3-methylbutanoic acid (20.4 g, 0.2 mol), thionyl chloride (35.7 g, 0.3 mol) and DMF (0.5 ml) was heated at reflux for 2 h. The mixture was carefully concentrated in vacuo to give the crude acid chloride. A suspension of anhydrous aluminium chloride (15.4 g, 115 mmol) in dichloromethane (100 ml) was cooled to 0° C. and a solution of the above acid chloride in dichloromethane (50 ml) was added dropwise. The mixture was stirred for 15 min and a solution of benzene (17.9 g, 0.23 mol) in dichloromethane (50 ml) was added dropwise and the resulting mixture stirred at room temperature for 16 h. The reaction mixture was poured into cold 0.05N hydrochloric acid (300 ml) and the resulting mixture extracted with dichloromethane (3×100 ml). The combined organic phases were washed with 1 hydrochloric acid (300 ml), water (300 ml) and saturated sodium hydrogen-carbonate solution (300 ml) and dried (MgSO$_4$). The solvent was evaporated in vacuo to give 21.6 g of 3-methylbutyrophenone.

A mixture of the above ketone (20.6 g, 127 mmol), hydroxylammonium chloride (17.7 g, 254 mmol) and absolute ethanol (200 ml) was heated at reflux for 1 h and then stirred at ambient temperature for 16 h. The solvent was evaporated in vacuo. The residue was suspended in water (200 ml) and the resulting mixture was extracted with dichloromethane (2×100 ml). The combined organic phases were washed with water (50 ml) and brine (10 ml) and dried (MgSO$_4$). The solvent was evaporated in vacuo to give 20.6 g of 3-methylbutyrophenone oxime.

A mixture of the above oxime (5.0 g, 28 mmol), 1,2-dibromoethane (25 ml) and N,N,N,N-tetrabutylammonium-bromide (1.0 g, 3 mmol) was cooled to 0° C. and 9N sodium hydroxide (35 ml) was carefully added. The mixture was stirred vigorously at room temperature for 3 days. Water (50 ml) was added and the resulting mixture extracted with dichloromethane (2×100 ml). To the combined organic phases was added water (50 ml) and pH in the aqueous phase was adjusted to 5 with 10% aqueous citric acid. The organic phase was washed with water (50 ml) and brine (50 ml) and dried (MgSO$_4$). The solvent was evaporated in vacuo to give 8.0 g of 3-methylbutyrophenone O-(2-bromoethyl)oxime.

A mixture of the above bromide (5.0 g, 18 mmol), (R)-3-piperidinecarboxylic acid ethyl ester (5.7 g, 36 mmol), potassium carbonate (7.5 g, 54 mmol), sodium iodide (0.3 g, 2 mmol) and acetone (150 ml) was heated at reflux for 16 h. Water (50 ml) was added and the volume reduced to one third in vacuo. The mixture was extracted with dichloromethane (2×100ml), the combined organic phases were dried (MgSO$_4$) and the solvent was evaporated in vacuo. The residue was purified by column chromatography on silica gel (80 g, noheptane/ethyl acetate 5/1) to give 3.6 g (R)-1-(2-(((1-phenyl-3-methyl-1-butylidene)amino)oxy) ethyl)-3-piperidinecarboxylic acid ethyl ester.

The above ester (3.6 g) was dissolved in ethanol (25 ml) and 2N sodium hydroxide (25 ml) was added and the mixture was heated at reflux for 30 min. The ethanol was evaporated in vacuo, pH in the residue was adjusted to 2 with 4N hydrochloric acid and the mixture was extracted with dichloromethane (2×25 ml). The combined organic phases were dried (MgSO$_4$) and the solvent was evaporated in vacuo. This afforded 3.4 g of the title compound.

$^1$H-NMR (DMSO-d$_6$) δ 4.65 ppm (m,2H).

EXAMPLE 15

(R)-1-(2-(((1,2-Bis(4-fluorophenyl)ethylidene)amino)oxy)ethyl)-3-piperidinecarboxylic acid hydrochloride A mixture of potassium cyanide (2.0 g, 31 mmol), 4-fluorobenzaldehyde, 96% ethanol (30 ml) and water (30 ml) was heated at reflux for 0.5 h and then kept at 5° C. for 72 h. The precipitated compound was collected and recrystallised from ethanol/water to give 20 g of 2-hydroxy-1,2-bis(4-fluorophenyl)ethanone.

A mixture of the above hydroxyketone (20.0 g, 81 mmol), powdered tin (18.0 g, 149 mol), concentrated hydrochloric acid (25 ml) and 96% ethanol (30 ml) was heated at reflux for 6 h. The reaction mixture was filtered hot and the filtrate cooled to 0° C. The precipitated compound was collected and recrystallised from 96% ethanol (50 ml) to give 10 g 1,2-bis(4-fluorophenyl) ethanone.

A mixture of the above ketone (4.8 g, 21 mmol), hydroxylammonium chloride (2.8 g, 40 mmol) and absolute ethanol (50 ml) was heated at reflux for 4 h and then stirred at room temperature for 16 h. Water (200 ml) was added and the resulting mixture extracted with dichloromethane (2×100 ml). The combined organic phases were washed with water (2×100 ml) and brine (100 ml) and dried (MgSO$_4$). The solvent was evaporated in vacuo to give 5.0 g of 1,2-bis(4-fluorophenyl)ethanone oxime.

To a mixture of the above oxime (5.0 g, 20 mmol), 1,2-dibromoethane (18 ml) and N,N,N,N-tetrabutylammonium bromide (0.61 g, 3 mmol) was carefully added 12N sodium hydroxide (19 ml) while the temperature was kept below 35° C. After stirring at ambient temperature for 17 h, water (50 ml) was added and the resulting mixture was extracted with dichloromethane (2×100 ml). Water (100 ml) was added to the combined organic phases and pH in the aqueous phase was adjusted to 5 with 10% citric acid. The organic phase was washed with water (50 ml) and brine (10 ml) and dried (MgSO$_4$). The solvent was evaporated in vacuo and the residue purified by column chromatography on silica gel (100 g, gradient n-heptane to n-heptane/ethyl acetate 20/1) to give 4.7 g of 1,2-bis(4-fluorophenyl)ethanone O-(2-bromoethyl)oxime.

A mixture of the above bromide (4.5 g, 13 mmol), (R)-3-piperidinecarboxylic acid ethyl ester (4.1 g, 26 mmol), potassium carbonate (5.4 g, 39 mmol), sodium iodide (0.2 g, 1 mmol) and acetone (100 ml) was heated at reflux for 16 h. Water (50 ml) was added, the volume was reduced to ⅓ in vacuo and the resulting mixture was extracted with dichloromethane (2×100 ml). The combined organic phases were dried (MgSO$_4$). The solvent was evaporated in vacuo and the residue was purified by column chromatography on silica gel (60 g, n-heptane/ethyl acetate 5/1) to give 3.6 g (R)-1-(2-(((1,2-bis(4-fluorophenyl)ethylidene)amino)oxy)ethyl)-3-piperidinecarboxylic acid ethyl ester.

The above ester (3.6 g, 84 mmol) was dissolved in a mixture of absolute ethanol (40 ml), 6N sodium hydroxide (7.0 ml) and water (10 ml) and heated at reflux for 0.5 h. The volume was reduced to ⅓ in vacuo, the resulting mixture was extracted with n-heptane (10 ml) and pH in the aqueous phase was adjusted to 2 with 4N hydrochloric acid. The aqueous phase was extracted with dichloromethane (2×25 ml), the combined organic phases were dried (MgSO$_4$) and the solvent was evaporated in vacuo. This afforded 3.5 g of the title compound.

$^1$H-NMR (CDCl$_3$) δ 4.05 (s,2H).

EXAMPLE 16

(R)-1-(2-((((1-Phenylcyclopent-1-yl)methylene)amino)oxy)ethyl)-3-piperidinecarboxylic acid hydrochloride To a solution of 1-phenyl-1-cyclopentanecarbonitrile (7.0 g, 41 mmol) in n-heptane (100 ml) cooled to −30° C. was dropwise added a 1M solution of diisobutylaluminium hydride in n-heptane (82 ml, 82 mmol). The mixture was stirred at −30° C. for 1 h and at 0° C. for 1 h. The mixture was diluted with diethylether (100 ml) and silica gel (60 g) was carefully added keeping the temperature below −30° C. The mixture was then allowed to warm to room temperature and then stirred for 20 h. After filtration the filtrate was washed with water (2×100 ml) and dried (MgSO$_4$). The solvent was evaporated in vacuo to give 3.45 g of the crude 1-phenyl-1-cyclopentanecarboxaldehyde.

A mixture of the above aldehyde (3.4 g, 20 mmol) and hydroxylammonium chloride (2.9 g, 42 mmol) in a mixture of absolute ethanol (30 ml) and pyridine (3.3 g, 42 mmol) was heated at reflux for 2 h. The solvent was evaporated in vacuo, the residue was treated with absolute ethanol (50 ml) and the suspension filtered. The solvent was evaporated from the filtrate in vacuo and the residue crystallised from a 4/1 mixture of n-heptane and ethyl acetate to give 2.5 g of 1-phenyl-1-cyclopentanecarboxaldehyde oxime.

A mixture of the above oxime (2.3 g, 12 mmol), (R)-1-(2-bromoethyl)-3-piperidinecarboxylic acid ethyl ester hydrobromide (4.2 g, 12 mmol), potassium carbonate (5.0 g, 36 mmol) and acetone (50 ml) was stirred at room temperature for 7 days. The mixture was filtered and the solvent was evaporated from the filtrate in vacuo. The residue was purified by column chromatography on silica gel (250 g, n-heptane/ethyl acetate ⅘) to give 0.69 g of (R)-1-(2-((((2-phenylcyclopent-1-yl)methylene)amino)oxy)ethyl)-3-piperidinecarboxylic acid ethyl ester.

The above ester (0.69 g, 1.85 mmol) was dissolved in a mixture of 96% ethanol (5 ml) and 4N sodium hydroxide (1.4 ml) and stirred at ambient temperature for 4 h. The reaction mixture was evaporated in vacuo, dichloromethane (100 ml) and concentrated hydrochloric acid (0.62 ml) was added. The mixture was washed with water (5 ml), dried (MgSO$_4$) and the solvent evaporated in vacuo. The residue was crystallised from acetone. This afforded 0.29 g of the title compound as a solid. M.p. 147°–149° C.

Calculated for C$_{20}$H$_{20}$N$_2$O$_3$·HCl·1.5 H$_2$O
C,58.9%;H,7.9%;N,6.9%; Found:
C,58.9%;H,7.3%;N,6.8%.

EXAMPLE 17

(R)-1-(2-(((1,2-Bis(2-fluorophenyl)ethylidene)amino)oxy)ethyl)-3-piperidinecarboxylic acid hydrochloride A mixture of potassium cyanide (2.0 g, 31 mmol), 2-fluorobenzaldehyde (26 g, 21 mmol), ethanol (30 ml) and water (30 ml) was heated at reflux for 1.5 h and then kept at −15° C. for 2 h. The precipitated compound was collected to give 20 g of 2-hydroxy-1,2-bis(2-fluorophenyl)ethanone.

A mixture of the above hydroxyketone (20.0 g, 81 mmol), powdered tin (18.0 g, 149 mol), concentrated hydrochloric acid (25 ml) and ethanol (30 ml) was heated at reflux for 3 h. The reaction mixture was filtered hot and the filtrate cooled to 0° C. The precipitated compound was collected and recrystallised from 96% ethanol (30 ml) to give 10 g 1,2-bis(2-fluorophenyl)ethanone.

A mixture of the above ketone (7.0 g, 30 mmol), hydroxylammonium chloride (3.2 g, 46 mmol) and 96% ethanol (100 ml) was heated at reflux for 3 h and then stirred at room temperature for 16 h. The reaction mixture was filtered and dried in vacuo to give 7.0 g of 1,2-bis(2-fluorophenyl)ethanone oxime.

To a mixture of the above oxime (7.0 g, 29 mmol), 1,2-dibromoethane (50 ml) and N,N,N,N-tetrabutylammonium bromide (1.0 g, 3 mmol) was carefully added 9N sodium hydroxide (33 ml) while the temperature was kept below 20° C. After stirring at ambient temperature for 3 h the phases were separated and the organic phase was washed with water (2×100 ml) and saturated aqueous ammonium chloride (30 ml). The solvent was evaporated in vacuo and the residue co-evaporated in vacuo with absolute ethanol (100 ml) to give 8.1 g of 1,2-bis(2-fluorophenyl)ethanone O-(2-bromoethyl)oxime.

A mixture of the above bromide (8.0 g, 23 mmol), (R)-3-piperidinecarboxylic acid ethyl ester tartrate (10.0 g, 33 mmol), potassium carbonate (4.5 g, 33 mmol), sodium iodide (4.0 g, 27 mmol) and acetone (100 ml) was heated at reflux for 24 h. The reaction mixture was filtered and the solvent was evaporated from the filtrate in vacuo. The residue was dissolved in diethyl ether (200 ml) and washed with water (2×100 ml). The solvent was evaporated in vacuo and the residue purified by column chromatography on silica gel (80 g, n-heptane/ethyl acetate 5/1) to give 2.5 g (R)-1-(2-(((1,2-bis(2-fluorophenyl)ethylidene)amino)oxy)ethyl)-3-piperidinecarboxylic acid ethyl ester.

The above ester (2.5 g, 6 mmol) was dissolved in a mixture of 96% ethanol (25 ml) and water (25 ml) and pH adjusted to 14 with 9N sodium hydroxide. The resulting mixture was heated at 50° C. for 1 h, cooled to ambient temperature, concentrated to 25 ml, washed with diethylether (2×50 ml) and pH adjusted to 2.5 with 6N hydrochloric acid. The mixture was extracted with dichloromethane (2×25 ml) and the solvent was evaporated in vacuo. This afforded 1.2 g of the title compound.

$^1$H-NMR (CDCl$_3$) δ 4.10 (s,2H).

We claim:

1. A compound of formula I

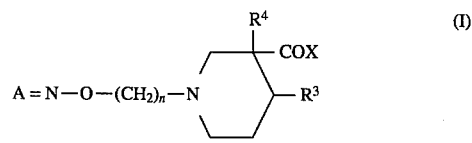

wherein
A is

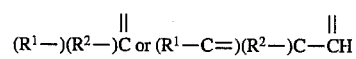

wherein one of R$^1$ and R$^2$ is hydrogen; C$_{1-4}$-alkoxy-$_{1-8}$-alkyl; straight or branched C$_{1-8}$-alkyl optionally substituted with either one to three halogen(s) or phenyl; C$_{3-7}$-cycloalkyl or C$_{3-7}$-cycloalkenyl, each of which is optionally substituted with phenyl; or phenyl; wherein each phenyl is optionally substituted with halogen, C$_{1-4}$-alkyl, C$_{1-4}$-alkoxy or trifluoromethyl; and the other of R$^1$ and R$^2$ is hydrogen; C$_{1-4}$-alkoxy-C$_{1-8}$-alkyl; straight or branched C$_{1-8}$-alkyl optionally substituted with either one to three halogen(s) or phenyl; C$_{3-7}$-cycloalkyl or C$_{3-7}$-cycloalkenyl, each of which is optionally substituted with phenyl; wherein each phenyl is optionally substituted with halogen, C$_{1-4}$-alkyl, C$_{1-4}$-alkoxy or trifluoromethyl;

R$^3$ and R$^4$ are hydrogen or together represent a bond;

X is hydroxy or C$_{1-4}$-alkoxy; and n is 2, 3, 4 or 5; or a pharmaceutically acceptable salt thereof.

2. A compound according to claim 1, wherein R$^3$ and R$^4$ are hydrogen.

3. A compound according to claim 1, wherein A is (R$^1$—C=)(R$^2$—)C—CH.

4. A compound according to claim 1, wherein A is (R$^1$—)(R$^2$—)C.

5. A compound according to claim 1, wherein one of $R^1$ and $R^2$ is hydrogen; $C_{1-4}$-alkoxy-$C_{1-8}$-alkyl; straight or branched $C_{1-8}$-alkyl optionally substituted with one to three halogen(s); $C_{3-7}$-cycloalkyl or $C_{3-7}$-cycloalkenyl, each of which is optionally substituted with phenyl; or phenyl; wherein each phenyl is optionally substituted with halogen, $C_{1-4}$-alkyl, $C_{1-4}$-alkoxy or trifluoromethyl; and the other of $R^1$ and $R^2$ is hydrogen; $C_{1-4}$-alkoxy-$C_{1-8}$-alkyl; straight or branched $C_{1-8}$-alkyl optionally substituted with one to three halogen(s); $C_{3-7}$-cycloalkyl or $C_{3-7}$-cycloalkenyl, each of which is optionally substituted with phenyl; wherein each phenyl is optionally substituted with halogen, $C_{1-4}$-alkyl, $C_{1-4}$-alkoxy or trifluoromethyl.

6. A compound according to claim 1 which is

E-(R)-1-(2-((((2-Methylphenyl)methylene)amino)oxy)ethyl)-3-piperidinecarboxylic acid;

(R)-1-(2-((((4-Methyl-2-phenyl-2-penten-1-ylidene)amino)oxy)ethyl)-3-piperidinecarboxylic acid;

Z-(R)-1-(2-(((1-Phenyl-1-octanylidene)amino)oxy) ethyl)-3-piperidinecarboxylic acid;

E-(R)-1-(2-(((1-Phenyl-1-octanylidene)amino)oxy) ethyl)-3-piperidinecarboxylic acid;

Z-(R)-1-(2-(((2-Methoxy-1-phenyl-1-ethylidene)amino)oxy)ethyl)-3-piperidinecarboxylic acid;

Z-(R)-1-(2-(((1-Phenyl-2,2,2-trifluoro-1-ethylidene)amino)oxy)ethyl)-3-piperidinecarboxylic acid;

(R)-1-(2-((((2-Phenyl-2-penten-1-ylidene)amino)oxy) ethyl)-3-piperidinecarboxylic acid;

(R)-1-(2-((((5-Methyl-2-phenyl-2-hexen-1-ylidene)amino)oxy)ethyl)-3-piperidinecarboxylic acid;

(R)-1-(2-(((5-Methoxy-1-phenyl-1-pentylidene)amino)oxy)ethyl)-3-piperidinecarboxylic acid;

(R)-1-(2-(((1-Phenyl-3-methyl-1-butylidene)amino)oxy) ethyl)-3-piperidinecarboxylic acid; or a pharmaceutically acceptable salt thereof.

7. A compound according to claim 1 which is

Z-(R)-1-(2-(((1-(Cyclopenten-1-ylphenylmethylene)amino)oxy)ethyl)-3-piperidinecarboxylic acid;

(R)-1-(2-((((Cyclopropylphenylmethylene)amino)oxy)ethyl)3-piperidinecarboxylic acid;

(R)-1-(2-(((((1-Phenylcyclopent-1-yl)methylene)amino)oxy)ethyl)-3-piperidinecarboxylic acid; or a pharmaceutically acceptable salt thereof.

8. A compound according to claim 1 which is (R)-1-(2-(((1,2-Diphenylethylidene)amino)oxy)ethyl)-3-piperidinecarboxylic acid;

(R)-1-(2-(((1,3-Diphenylprop-2-ylidene)amino)oxy)ethyl)-3-piperidinecarboxylic acid;

(R)-1-(2-(((1,2-Bis(4-fluorophenyl)ethylidene)amino)oxy)ethyl)-3-piperidinecarboxylic acid;

(R)-1-(2-(((1,2-Bis(2-fluorophenyl)ethylidene)amino)oxy)ethyl)-3-piperidinecarboxylic acid; or a pharmaceutically acceptable salt thereof.

9. A pharmaceutical composition comprising a compound according to claim 1 together with a pharmaceutically acceptable carrier or diluent.

10. The pharmaceutical composition according to claim 9, wherein the compound is present in amount between 0.5 mg and 1000 mg per unit dose.

11. A method of treating a central nervous system ailment related to the GABA uptake in a subject in need of such treatment comprising administering to said subject an effective amount of a compound according to claim 1.

12. A method of treating a central nervous system ailment related to the GABA uptake in a subject in need of such treatment comprising administering to said subject an effective amount of a pharmaceutical composition according to claim 9.

* * * * *